US012599320B2

(12) United States Patent
Yang

(10) Patent No.: US 12,599,320 B2
(45) Date of Patent: Apr. 14, 2026

(54) MICRO ANALYTE SENSOR AND CONTINUOUS ANALYTE MONITORING DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 249 days.

(21) Appl. No.: 18/576,092

(22) PCT Filed: Aug. 6, 2021

(86) PCT No.: PCT/CN2021/111221
§ 371 (c)(1),
(2) Date: Jan. 2, 2024

(87) PCT Pub. No.: WO2023/010539
PCT Pub. Date: Feb. 9, 2023

(65) Prior Publication Data
US 2024/0324912 A1      Oct. 3, 2024

(51) Int. Cl.
| | |
|---|---|
| *A61B 5/145* | (2006.01) |
| *A61B 5/00* | (2006.01) |
| *A61B 5/1495* | (2006.01) |

(52) U.S. Cl.
CPC ........ *A61B 5/14546* (2013.01); *A61B 5/1495* (2013.01); *A61B 5/7214* (2013.01); *A61B 2562/028* (2013.01)

(58) Field of Classification Search
CPC ............ A61B 5/14532; A61B 5/14865; A61B 5/6849; A61B 5/7214; A61B 5/1495; A61B 5/14546; A61B 2562/028
(Continued)

(56) References Cited

U.S. PATENT DOCUMENTS

| | | | |
|---|---|---|---|
| 2005/0264302 A1 | 12/2005 | Mohajer et al. | |
| 2008/0086044 A1* | 4/2008 | Brister ............... | A61B 5/14532 |
| | | | 600/365 |

(Continued)

FOREIGN PATENT DOCUMENTS

| | | |
|---|---|---|
| CN | 103293198 | 9/2013 |
| CN | 105759714 | 7/2016 |

(Continued)

OTHER PUBLICATIONS

"International Search Report (Form PCT/ISA/210) of PCT/CN2021/111221", mailed on Apr. 26, 2022, pp. 1-2.

*Primary Examiner* — Igor N Borissov
(74) *Attorney, Agent, or Firm* — JCIP GLOBAL INC.

(57) ABSTRACT

A micro analyte sensor includes a substrate, which includes an internal part and an external part; a first electrode group and a second electrode group, located on the surface of the internal part, each electrode group including at least one working electrode and at least one additional electrode. The external part is provided with pins corresponding to each electrode, the pins are respectively electrically connected with the working electrode and the additional electrode through wires. The first electrode group detects the analyte at the first frequency and provides the first detection signal, and the second electrode group detects the analyte at the second frequency and provides the redundant detection signal, and the first frequency is not less than the second frequency.

9 Claims, 3 Drawing Sheets

(58) Field of Classification Search
USPC .......................................................... 600/301
See application file for complete search history.

(56)                   References Cited

U.S. PATENT DOCUMENTS

2019/0175079 A1*   6/2019   Nishida ................ A61B 5/1495
2020/0178801 A1    6/2020   Nazari et al.
2020/0205694 A1*   7/2020   Bohm ................ A61B 5/14865

FOREIGN PATENT DOCUMENTS

| CN | 109212539 | 1/2019 |
| CN | 111479504 | 7/2020 |
| CN | 113033722 | 6/2021 |

* cited by examiner

MICRO ANALYTE SENSOR AND CONTINUOUS ANALYTE MONITORING DEVICE

CROSS-REFERENCE TO RELATED APPLICATION

This application is a 371 of international application of PCT application serial no. PCT/CN2021/111221, filed on Aug. 6, 2021. The entirety of the above mentioned patent application is hereby incorporated by reference herein and made a part of this specification.

TECHNICAL FIELD

The invention mainly relates to the field of medical devices, in particular to a micro analyte sensor.

BACKGROUND

The pancreas in a normal human body can automatically monitor the level of glucose in the human blood and automatically secrete the required insulin/glucagon. In diabetics, the pancreas does not function properly and cannot produce the insulin the body needs. Therefore, diabetes is a metabolic disease caused by abnormal pancreatic function, and diabetes is a lifelong disease. At present, there is no cure for diabetes with medical technology. The occurrence and development of diabetes and its complications can only be controlled by stabilizing blood glucose.

Diabetics need to have their blood glucose measured before they inject insulin into the body. At present, most of the testing methods can continuously measure blood glucose and send the data to a remote device in real time for the user to view. This method is called Continuous Glucose Monitoring (CGM). The method requires the device to be attached to the skin and the probe it carries is inserted into the tissue fluid beneath the skin.

However, at present, the analyte sensor adopts single electrode group to obtain parameter information, which is prone to detection signal distortion or failure and low reliability.

Therefore, a highly reliable micro analyte sensor is urgently needed in the current technology.

BRIEF SUMMARY OF THE INVENTION

In view of the above the disadvantages of existing technology, the first aspect of the embodiment of the invention discloses a micro analyte sensor, including the first electrode group and the second electrode group, decorate in the sensor substrate, the first electrode group provides the first detection signal at the first frequency, the second electrode group provides redundant detection signals at the second frequency, improve service reliability, enhance the user experience.

The invention discloses a micro analyte sensor, which comprises a base, which comprises an internal part and an external part; The first electrode group and the second electrode group, located on the surface of the internal part, each electrode group includes at least one working electrode and at least one additional electrode; In the external part is provided with pins corresponding to each electrode, the pins are respectively electrically connected with the working electrode and the additional electrode through a wire; The first electrode group and the second electrode group are configured so that, when in use, the first electrode group provides the first detection signal at the first frequency, and the second electrode group provides the redundant detection signal at the second frequency, and the first frequency is not less than the second frequency.

According to one aspect of the invention, the additional electrode includes a counter electrode.

According to one aspect of the invention, the additional electrode also includes a reference electrode.

According to one aspect of the invention, the first electrode group and the second electrode group include two working electrodes.

According to one aspect of the invention, the first frequency is 6~3600 times/h and the second frequency is 0.01~60 times/h.

According to one aspect of the invention, the first frequency is an integer multiple of the second frequency.

According to one aspect of the invention, the area of the first electrode group is not less than that of the second electrode group.

According to one aspect of the invention, when the life of the first electrode group is prematurely terminated, the second electrode group switches to the first frequency and succeeds in providing the detection signal.

Compared with the prior art, the technical scheme of the invention has the following advantages:

The invention discloses micro analyte sensor, in the setting of the body part of the substrate has a first electrode and a second electrode group, each group includes at least one electrode working electrode and at least one additional electrode, at least two working electrodes and two additional electrodes are arranged on the sensor, electrode through a wire and set up some corresponding pins in vitro electrical connection. The first electrode group provides the first detection signal at the first frequency, and the second electrode group provides the redundant detection signal at the second frequency, when the first detection signal is distorted or invalid due to excessive background noise, the sensor can still output redundant detection signal as the detection signal of analyte, and avoid the window period of analyte detection signal, and thus could improve sensor reliability and user experience.

Further, the first frequency is not less than the second frequency. When the first detection signal is normally provided, the analyte detection signal is provided with a higher first frequency to meet user experience. The second frequency is slightly lower, which can slow down the sensitivity decline rate of the second electrode group to provide redundant detection signals with high confidence.

Furthermore, the first frequency is an integer multiple of the second frequency. While the second electrode group provides redundant detection signals, the first electrode group provides the first detection signal, preventing the time difference between the two electrode groups to provide signals, wiring to inconsistent detection environment, and improving detection reliability.

Further, the micro analyte sensor disclosed in the invention can be divided into a three-electrode system and a two-electrode system, wherein the three-electrode system is a counter electrode, a reference electrode and at least one working electrode, and the two-electrode system is a counter electrode and at least one working electrode. In addition, according to the number of working electrodes, the invention can also be divided into two cases: 1) single working electrode: there is only one working electrode; 2) Dual-working electrode: There are two working electrodes. One of them reacts with the analyte in an electric REDOX reaction to produce an electrical signal, which is called the "working electrode". The other is usually responsible for detecting the response signal of the interferometer or background solution, which is called the "auxiliary electrode". All of the above electrode compositions have their unique advantages. The three-electrode system has an extra reference electrode, which can effectively control the detection potential, prevent potential drift and improve the reliability of the parameter information of the detection analyte. However, the two-electrode system has simpler structure and lower production cost.

Further, the area of the first electrode group is not less than that of the second electrode group, and the area is reasonably allocated according to the use frequency of the electrode group, so that the service life of the first electrode group is consistent with that of the second electrode group.

Further, redundancy test signal is also used to calibration/diagnosis first detection signal, with the use of the first electrode group, its sensitivity decreases with time, and the detection parameters need to be adjusted at real-time, on the other hand, when oxygen concentration changes in the host or enzyme deficiency on the sensor, the second electrode configuration were used to detect data can be real-time calibration or diagnosis to the first electrode group, make the first electrode group maintain high reliability detection state.

Further, when the life of the first electrode group is prematurely terminated, the second electrode group switches to the first frequency and takes over the first electrode group to provide detection signals to extend the service life of the sensor and enhance the user experience.

The second aspect of the embodiment of the invention discloses a continuous analyte monitoring device, including: a bottom case for mounting on the skin surface of the host; The sensor unit comprises a base and at least one micro analyte sensor as mentioned above. The micro analyte sensor is fixed on the base and the sensor unit is mounted on the bottom case through the base to provide the analyte detection signal in the host body; The transmitter unit comprises an internal circuit, a transmitter and an electrical connection area, the electrical connection area and the sensor unit are electrically connected, the internal circuit triggers the electrode group according to a predetermined frequency, and the transmitter is used to send the analyte parameter information to the outside world; Batteries, which provide electricity; And the receiver, the receiver is used to receive the detection signal and indicate to the user.

The reliability of the sensor is often the key factor limiting the reliability of the continuous analyte monitoring device. Now, the first electrode group and the second electrode group are set. The first electrode group provides the first detection signal and the second electrode group provides the redundant detection signal to enhance the reliability of the sensor detection signal. The redundant detection signal can also be used to calibrate or diagnose the first detection signal. At the same time, when the life of the first electrode group is prematurely terminated, the second electrode group can take over to provide the detection signal, further improving the reliability of the sensor.

DETAILED DESCRIPTION

Figure 1:
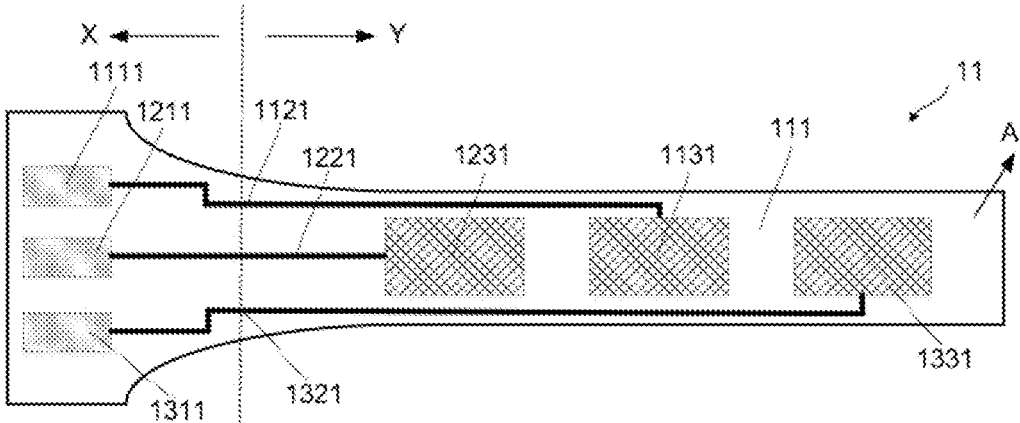
FIG. 1 is a top view of the sensor according to an embodiment of the invention.

As previously mentioned, prior art analyte sensors using a single electrode group, excessive background noise in the host body, reduced electrode sensitivity, or premature termination of electrode life can result in distortion or failure of the sensor detection signal and reduced reliability.

In order to solve the problem, the present invention provides a micro analyte sensor, is set in the internal part of the sensor substrate has a first electrode group and a second electrode group, each group includes at least one electrode working electrode and at least one additional electrode, since all of the electrode group have been stabbed into the host, there is no hot swap process, and each electrode body fluid environment is consistent, each electrode group is configured as when in use, the first electrode group provides the first detection signal at the first frequency, and the second electrode group provides the redundant detection signal at the second frequency, users can use the redundant detection signal as the replacement detection signal to continue to obtain the parameter information of the analyte in vivo in case of distortion or failure of the first detection signal, or use the redundant detection signal to calibrate/diagnose the first detection signal to improve the reliability of the measured analyte parameter data and enhance the user experience.

Various exemplary embodiments of the invention will now be described in detail with reference to the attached drawings. It shall be understood that the relative arrangement of parts and steps, numerical expressions and numerical values described in these embodiments shall not be construed as limiting the scope of the present invention unless otherwise specified.

In addition, it should be understood that, for the sake of description, the dimensions of the individual components shown in the attached drawings are not necessarily drawn to their actual proportions; for example, the thickness, width, length or distance of some elements may be magnified relative to other structures.

The following description of exemplary embodiments is only illustrative and does not in any sense constitute any limitation on the invention or its application or use. Techniques, methods and devices known to ordinary technicians in the relevant field may not be discussed in detail here, but to the extent applicable, they shall be considered part of this specification.

It should be noted that similar labels and letters indicate similar items in the appended drawings below, so that once an item has been defined or described in an appended drawing, no further discussion of it will be required in subsequent appended illustrations.

It is further understood that the one or more method steps mentioned in the invention do not preclude the existence of other method steps before and after the combined steps or the insertion of other method steps between those explicitly mentioned steps, unless otherwise stated; It should also be understood that the combined connection relationship between one or more devices/devices mentioned in the invention does not preclude the existence of other devices/devices before and after the combined devices/devices or the insertion of other devices/devices between these explicitly mentioned two devices/devices, unless otherwise stated. And, unless otherwise specified, the serial number of the steps just a convenient tool for identifying the steps, rather than to limit the steps of the order or limit the scope of the present invention can be implemented, the relationship of the relative change or adjust, in the case of no substantial changes to technical content, when as well as the category of the present invention can be implemented.

Figure 2:
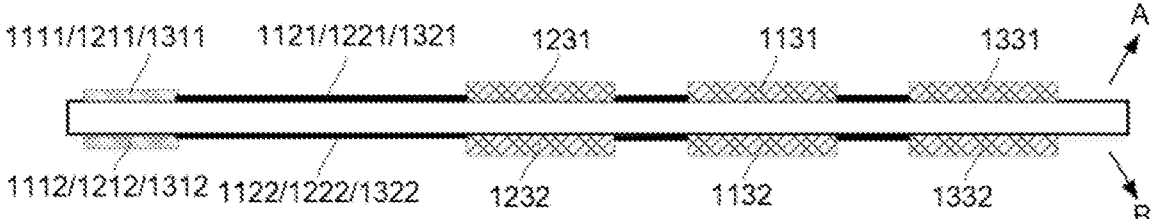
FIG. 2 is a side view of the sensor in an embodiment of FIG. 1.

FIG. 1 is a top view of the sensor in an embodiment of the invention; FIG. 2 is a side view of the sensor in an embodiment of FIG. 1.

Sensor 11 includes substrate 111, which is divided into an external part X and an internal part Y, with the dotted line shown in FIG. 1 as the dividing line. The internal part Y is covered with electrodes, including at least one working electrode 1131 and at least one additional electrode, obviously, in this example, additional electrodes include a counter electrode 1231 and a reference electrode 1331, which constitute three-electrodes system, the counter electrode 1231 is the other electrode relative to the working electrode 1131, and forms a closed loop with the working electrode 1131, so that the current on the electrode can normally conduct. The reference electrode 1331 is used to provide the reference potential of the working electrode 1131, so the detection potential can be effectively controlled. In another embodiment of the invention, additional electrode can only include the counter electrode 1231, so as to form a double-electrode system, compared to the three-electrode system, the effective area of working electrode 1131 and counter electrode 1231 can be increased on the finite area of the body part Y, so as to prolong the service life of the electrode, and because the reduced one electrode, the processing technology is more simple. However, without the detection potential of the reference electrode as a reference for the working electrode 1131, the reliability of the detection information of analytes will be reduced. In another embodiment of the invention, there are two working electrodes 1131, one of which generates an electrical signal by performing an electric redox reaction with the analyte to be detected, and the other is used to detect the response signal of interference or background solution in the host body fluid, and this electrode is an auxiliary electrode.

Continue referring to FIG. 1 and FIG. 2. The external part X is provided with pins, which correspond to the electrode one by one and are electrically connected through a wire, that is, the first pin 1111 corresponding to the working electrode 1131 is electrically connected through a wire 1121. The second pin 1211 corresponding to the counter electrode 1231 is electrically connected through the wire 1221; And the third pin 1311 corresponding to the reference electrode 1331, electrically connected through the wire 1321. Different pins, wires and electrodes are insulated from each other to prevent electrical signals from being tampered with.

Because sensor 11 is planar, there are two opposite surfaces, namely surface A and surface B. Working electrode 1131, counter electrode 1231 and reference electrode 1331 are laid on surface A of the sensor as the first electrode group 31, in contrast, on the surface B of the sensor, laying a second electrode group, the electrode configuration can be a double electrode system, can also be a three electrode system, also can be double work electrode, optimization, consistent with A surface electrode group, That is, including the working electrode 1132, counter electrode 1232 and reference electrode 1332, similarly, the surface B is also laid with a pin, the pins correspond one to one to the electrodes on the surface B, and through the wire electrical connection, that is, the fourth pin 1112 corresponding to the working electrode 1132, through the wire 1122 electric connection; The fifth pin 1212 corresponding to the counter electrode 1232 is electrically connected through the wire 1222; And the sixth pin 1312 corresponding to the reference electrode 1332 is electrically connected through the wire 1322. In this way, when the life of any electrode of the first electrode group 31 on surface A terminates or fails prematurely, the same name electrode of the second electrode group 32 on surface B can be switched to the same working frequency as that of the first electrode group and enter the working state in place of it, so as to improve the reliability of parameter data of analyte detection and extend the service life of the sensor.

Technical personnel in this field should understand that there is no restriction on the sequence and position of pins, wires and electrodes laid on either surface A or surface B of the sensor. The pins, wires, and electrodes on both surfaces may be arranged symmetrically or asymmetrically. The corresponding pins, wires and electrodes are laid on the same surface or on different surfaces. Preferably, the corresponding pins, wires and electrodes are laid on the same surface to facilitate the wiring of the wires. For example, the working electrode 1131 on surface A can be replaced with the counter electrode 1231, or the counter electrode 1231 on surface A can be replaced with the reference electrode 1332 on surface B, no matter how the sequence and position of the pins, wires and electrodes on surface A and B changed, it is necessary to make the pins, wires and electrodes correspond to each other and insulate each other.

In other embodiments of the present invention, the service life of the sensor can be further increased by increasing the sensor area or reducing the electrode area to increase the number of electrode sets, even though there are only relative surface A and surface B of the planar structure sensor. However, too large sensor area may increase the rejection reaction of the host and cause the discomfort of the host. Too small electrode area will reduce the sensitivity of the electrode and reduce the reliability of the detection parameters. Excessive number of electrode groups will also increase the complexity of the processing process, such as the wire routing will become very dense. Therefore, the preferred number of electrode group is two.

In other embodiments of the invention, the groups of electrodes may also be distributed on the same side of the sensor, such as surface A or surface B, where no restrictions are imposed.

In other embodiments of the invention, the sensor may also be of a cylindrical or conical structure, with the electrodes arranged on the substrate surface in a wraparound manner.

In the embodiment of the invention, the substrate 111 is a material with excellent insulating properties, mainly from inorganic nonmetallic ceramics, silica glass and organic high polymer, etc. At the same time, considering the application environment of the implantable electrode, the base material is also required to have high impermeability and mechanical strength. Preferably, the substrate material is selected from one or more combinations of polytetrafluoroethylene (Teflon), polyethylene (PE), polyvinyl chloride (PVC), acrylonitrile butadiene-styrene copolymer (ABS), polymethyl methacrylate (PMMA), polycarbonate (PC), polyimide (PI) and so on.

Figure 3:
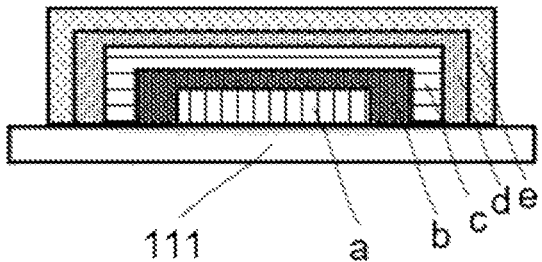
FIG. 3 is a sectional view of the electrode according to an embodiment of the invention.

FIG. 3 shows a sectional view of the electrode. In one embodiment of the invention, the working electrode (auxiliary electrode), the counter electrode and the reference electrode at least include the electron conduction layer a, the anti-interference layer b, the enzyme layer c, the adjustment layer d and the biological compatibility layer e. And the anti-interference layer b, the enzyme layer c, the adjustment layer d and the biological compatibility layer e are collectively referred to as the membrane layer.

Electron Conduction Layer:

The electron conduction layer a is made of materials with good electrical conductivity and fortification inertia. Preferred, the working electrode and the counter electrode are selected from graphite electrode, glass carbon electrode, noble metal and other materials, the reference electrode is selected from one of Ag/AgCl or calomel. Considering the requirements of good ductility and stability of surface structure, noble metal electrodes, such as gold electrode, platinum electrode and silver electrode, become a better choice. The working electrode and counter electrode are both platinum electrode for further optimization.

In the patented technical solution, the micro structure is arranged in the electron conduction layer a.

Anti-Interference Layer:

The anti-interference layer b is located between the enzyme layer and the electron conduction layer. Interferers are molecules or substances that undergo electrochemical reduction or oxidation on the electrode surface, either directly or indirectly through an electron transfer agent, resulting in an erroneous signal that interferes with analyte detection. For example, for the determination of glucose as an analyte, common interferences in the body are urea, ascorbic acid, acetaminophen, and so on.

In the preferred example, the anti-interference layer b prevents one or more interference agents from penetrating the electrolyte surrounding the electrode. For example, the anti-interference layer b allows the analyte to be measured at the electrode (e. g., hydrogen peroxide) to pass through, while at the same time preventing the passage of other substances (e. g., potentially interfering substances). In a preferred scenario, the anti-interference layer b could be a very thin membrane designed to limit the diffusion of substances with molecular weights greater than 34 Da.

In another preferred example, the anti-interference layer b can be an organic polymer, which can be prepared from organosilane and a hydrophilic copolymer. Hydrophilic copolymers, preferably, polyethylene glycol (PEG), poly (2-hydroxyethyl methacrylate) and poly (lysine). In a preferred embodiment, the thickness of the anti-interference layer b may range from 0.1 um or less to 10 um or more. The preferred thickness range is 0.5 um to 5 um.

Enzyme Layer:

The enzyme layer c is coated with active enzymes. According to the type of analyte to be detected, the corresponding active enzymes are coated. Active enzymes can make the analyte to be detected produce some chemical reactions and generate electrons. According to different concentrations of analyte to be detected, the number of electrons produced is different, and the electrons are collected by the electron conduction layer, thus forming different current intensity. Therefore, current intensity information can be used to characterize the parameter information of the analyte.

Preferably, the enzyme layer c is coated with glucose oxidase (GOx).

Adjustment Layer:

The adjustment layer d is located above the enzyme layer. In the embodiment of the present invention, when the enzyme layer is coated with glucose oxidase, the adjustment layer d is mainly used to regulate the transmittance of oxygen and glucose transferred to the enzyme layer. The amount of glucose (molar concentration) in body fluids is one order of magnitude higher than the amount of oxygen. However, for enzymatic sensors that require oxygen, an excess oxygen supply is needed to ensure that oxygen does not become a limiting substance, so that the sensor can respond linearly to changes in glucose concentration without being affected by oxygen partial pressure. In other words, when oxygen content is the limiting factor, the linear range of glucose oxygen monitoring reaction does not reach the expected concentration range. Without a semi-permeable membrane above the enzyme layer to regulate the passage of oxygen and glucose, the upper limit of the sensor's linear response to glucose is only about 40 mg/dL. However, in a clinical setting, the upper limit of the linear response of blood glucose levels needs to be about 500 mg/dL.

Adjustment layer d acts primarily as a semi-permeable membrane to regulate the amount of oxygen and glucose transmitted to the enzyme layer and, more specifically, to make oxygen excess a non-limiting factor. The upper limit of the linear response of the sensor to glucose with the adjustment layer can be reached to a higher level than that without the adjustment layer. In a preferred example, the ratio of oxygen-glucose transmittance in adjustment layer d can be reached to 200:1, thus ensuring that sufficient oxygen is available for the enzymatic reaction at any glucose and oxygen concentration that may be present subcutaneally.

In one preferred example, the adjustment layer d may be an organic polymer, which may be prepared from organosilane and a hydrophilic copolymer. Hydrophilic copolymer, preferably, copolymerization or graft of polyethylene glycol (PEG). Other hydrophilic copolymers that may be used include, but are not limited to, other diols such as propylene glycol, esters, amides, carbonates, and polypropylene glycol. The use of organosilicone polymers can obviously improve the oxygen transmission, and effectively control the glucose transmission. In a preferred implementation, the adjustment layer d may be in the thickness range of 1 um or less to 50 um or greater, with a preferred thickness range of 1 um to 10 um.

Biological Compatibility Layer:

The biocompatibility layer e is located at the outermost part of the electrode, which is designed to eliminate the body's rejection of foreign bodies and reduce the formation of a shielding cell layer around the implanted electrode.

In a preferred example, the biocompatibility layer e can be prepared from organosilanes and a hydrophilic copolymer. Hydrophilic copolymer, preferably, copolymerization or graft of polyethylene glycol (PEG). Other hydrophilic copolymers that may be used include, but are not limited to, other diols such as propylene glycol, esters, amides, carbonates, and polypropylene glycol.

In a preferred embodiment, the thickness of the biocompatibility layer e may range from 1 micron or less to 100 microns or more. A preferred thickness range is 10 um to 30 um.

In the embodiment of the invention, the thickness of base 11 is 0.01~0.8 mm, each electrode is rectangular, the width of each electrode is 0.01~1 mm, and the area is 0.1~2 mm$^2$.

In other embodiments of the present invention, the electron conduction layer a is also provided with a carbon nanotube modified layer (not shown in the FIG.). Using the unique mechanical strength, high specific surface area, fast electron transfer effect and chemical stability of carbon nanotubes, the carbon nanotubes are modified to the surface of the electron conduction layer a on the surface of the formed electron conduction layer a by means of physical adsorption, embedding or covalent bonding to improve the electron transfer speed. At the same time, because of its large specific surface area, it can be used as an excellent catalyst (enzyme) carrier. The modified carbon nanotube layer can be fixed on the surface of the electron conduction layer a by Nafion solution dispersion method, covalent fixation method, etc.

Figure 4:
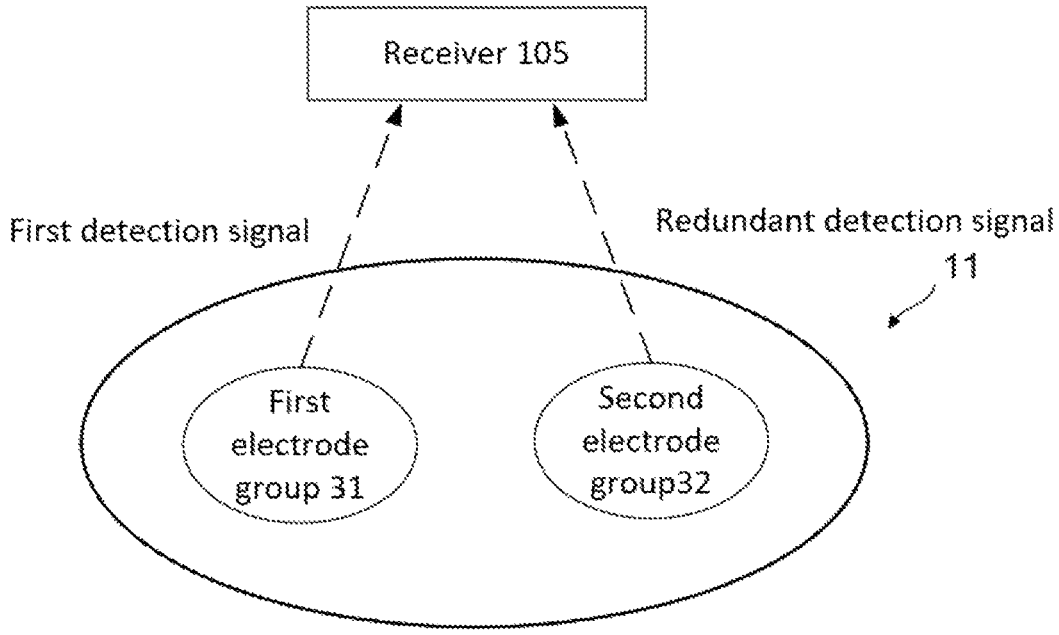
FIG. 4 is a schematic diagram of the system according to an embodiment of the invention.

FIG. 4 is a schematic diagram of an embodiment system of the invention.

After the sensor enters the host body, a voltage is applied to the pin, and the corresponding electrode of the pin is activated to enter the working state. That is, the first electrode group 31 on surface A (including working electrode 1131, counter electrode 1231 and reference electrode 1331) and the second electrode group 32 on surface B (including working electrode 1132, counter electrode 1232 and reference electrode 1332) are simultaneously activated after entering the host. The first electrode group 31 provides the first detection signal at the first frequency $f_1$, and the second electrode group 32 provides the redundant detection signal at the second frequency $f_2$. Both the first detection signal and the redundancy detection signal are sent to a device (such as receiver 105) that can be observed by the user. Under normal circumstances, the receiver 105 displays the first detection signal and the redundancy detection signal is not displayed to avoid confusion caused by the user reading the double signal. When sensor environment background noise is too big, or some electrodes reduced sensitivity to the first electrode group, or an early termination of electrode life, cause the distortion or failure of the first electrode group, the receiver 105 no longer displays the first detection signal of the first electrode group 31, but the redundant detection signal of the second electrode group 32, preventing the user from reading distorted or invalid detection data.

Optimization, the first frequency is not lower than the second frequency, the normal work of the electrode, the first electrode 31 with a higher frequency of the first group to provide the first detection signal, meet the demand of users daily test, the second electrode group 32 to provide redundancy lower second frequency signal, the sensitivity of slow attenuation, to maintain a high degree of confidence of redundancy detection.

In the preferred embodiment of the invention, the first frequency $f_1$ is 6~3600 times/h, and the second frequency $f_2$ is 0.01~60 times/h.

Further optimized, the first frequency $f_1$ is an integer multiple of the second frequency $f_2$. While the second electrode group 32 provides redundant signals, the first electrode group 31 can provide the first detection signal at the same time, so as to avoid the time difference of detection signals, resulting in inconsistent detection environment.

For further optimization, the first frequency $f_1$=30 times/h, and the second frequency $f_2$=10 times/h.

In other examples of the invention, the effective working time of the first electrode group after activation is 1~14 days, and after 14 days, the enzyme activity on the electrode decreases and enters the failure state. At the same time, there may be damage to the electrode or errors in the processing process, and the activated electrode will enter the failure state in advance. If a single electrode group is set on the sensor, once a certain electrode enters the failure state, the sensor will fail, and the user needs to replace the new sensor, which reduces the user experience and increases the user's use cost.

If multiple electrode groups are set on the sensor, for example, the first electrode group 31 and the second electrode group 32 are set, once a certain electrode in the first electrode group 31 enters the failure state, the working frequency of the same name electrode in the second electrode group 32 is changed to $f_1$ to replace the failed electrode in the first electrode group 31, the sensor can continue to work normally, prolong the service life of sensors, Improve detection reliability.

Specifically, refer to FIG. 1 and FIG. 2. After the sensor enters the host body, the first pin 1111, the second pin 1211 and the third pin 1311 on surface A and the third pin 1112, the fourth pin 1212 and the fifth pin 1312 on surface B are applied voltage by the internal circuit 1031 (see FIG. 5 for details). The working electrode 1131, counter electrode 1231 and reference electrode 1331 of surface A enter the working state at the frequency $f_1$, while the working electrode 1132, counter electrode 1232 and reference electrode 1332 of surface B enter the working state at the frequency $f_2$. If any electrode in working electrode 1131, counter electrode 1231 and reference electrode 1331 fails prematurely or its life ends, the internal circuit 1031 switches the pin object of applying voltage. For example, if working electrode 1131 fails prematurely, the internal circuit switches the frequency of applying voltage to the fourth pin 1112 on surface B. working electrodes on the surface B of the 1132 working frequency changes from $f_2$ to $f_1$, the new electrode group was combined with the counter electrode 1231 and the reference electrode 1331, which had not failed, to detect the analyte, so as to avoid the early failure of sensor 11, the user does not need to replace the sensor due to the early failure of the working electrode 1131, which enhances the user experience and reduces the cost of sensor replacement. In the embodiment of the invention, due to the frequency change of the working electrode 1132 on the second electrode group on surface B, the second electrode group 32 cannot continue to provide redundant detection signals, and the internal circuit 1031 no longer applies voltage to the other electrodes of the second electrode group 32 on surface B, and the other electrodes therefore enter the hibernation state.

It should be understood by technicians in this field that the above embodiments are not limited to the failure of the working electrode, and that the failure of other electrodes such as counter electrode, reference electrode, or two or three electrodes at the same time can be replaced by the method of using the same named electrode in the above embodiments.

In other embodiments of the invention, the array of electrodes on the sensor may be multiple and not limited to the first electrode group 31 and the second electrode group 32.

Figure 5:
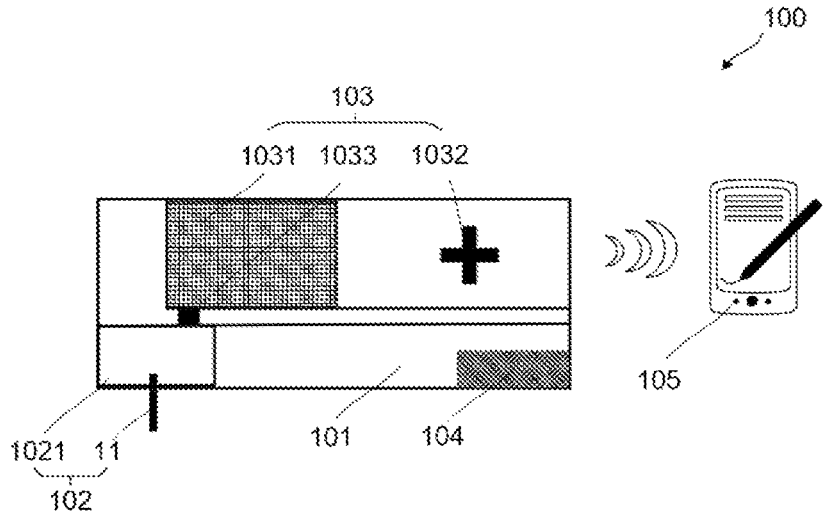
FIG. 5 is a schematic diagram of a continuous analyte monitoring device according to an embodiment of the invention.

FIG. 5 is a schematic diagram of the embodiment of continuous analyte monitoring device 100. Continuous analyte monitoring device 100 includes sump 101 for mounting on the host skin surface; The sensor unit 102 comprises a base 1021 and a micro analyte sensor 11 as described above. The micro analyte sensor 11 is fixed on the base, and the sensor unit 102 is installed on the bottom shell 101 through the base; The transmitter unit 103 comprises an internal circuit 1031, an transmitter 1032 and an electrical connection area 1033, which is electrically connected with the sensor unit 102. The internal circuit 1031 is used to apply voltage to each pin in accordance with the predetermined frequency, so that the corresponding electrode can detect the analyte in accordance with the frequency and provide detection signals; Transmitter 1032 is used to send analyte detection signals to the outside world; Battery 104, battery 104 is used to provide electricity; Receiver 105, receiver 105 is used to receive the analyte detection signal and indicate to the user.

To sum up, the invention discloses a kind of micro analyte sensor, is set in the internal part of the sensor substrate has a first electrode group and a second electrode group, each group includes at least one electrode working electrode and at least one additional electrode, the first electrode group and the second electrode group are configured for when in use, the first electrode group detects the analyte at the first frequency and provides the first detection signal, while the second electrode group detects the analyte at the second frequency to provide redundant detection signals. When the first detection signal is distorted or invalid, the user can read the redundant detection signal, which improves the reliability of the sensor and enhances the user experience.

The present invention also made public a kind of use as stated earlier the micro continuous analyte sensor analytes monitoring devices, due to the continuous analyte detection device reliability is often limited to the reliability of the sensor, micro analyte sensor adopted as stated earlier, can make the continuous analyte detection device to realize redundant detection, improves the detection reliability, prolong the service life of sensors, which enhances user experience and reduces user cost.

Although some specific embodiments of the present invention have been detailed by examples, those skilled in the field should understand that the above examples are for illustrative purposes only and not to limit the scope of the present invention. Persons skilled in this field should understand that modifications may be made to the above embodiments without separating them from the scope and spirit of the present invention. The scope of the invention is defined by the attached claims.

The invention claimed is:

1. A micro analyte sensor, comprising:

a substrate, including an internal part and an external part which are located on a same surface of the substrate;

a first electrode group and a second electrode group which are located on a surface of the internal part, wherein each of the first electrode group and the second electrode group comprises at least one working electrode and at least one additional electrode, wherein the external part is provided with pins corresponding to the working electrode and the additional electrode, and the pins are respectively electrically connected with the working electrode and the additional electrode through wires, wherein the first electrode group detects an analyte at a first frequency and provides a detection signal, and the second electrode group detects the analyte at a second frequency to provide a redundant detection signal, and the first frequency is not less than the second frequency.

2. According to the micro analyte sensor mentioned in claim 1, wherein the at least one additional electrode includes a counter electrode.

3. According to the micro analyte sensor mentioned in claim 2, wherein the at least one additional electrode includes a reference electrode.

4. According to the micro analyte sensor mentioned in claim 1, wherein the at least one working electrode of each of the first electrode group and the second electrode group comprises two working electrodes.

5. According to the micro analyte sensor mentioned in claim 1, wherein the first frequency is 6~3600 times/h, and the second frequency is 0.01~60 times/h.

6. According to the micro analyte sensor mentioned in claim 5, wherein the first frequency is an integer multiple of the second frequency.

7. According to the micro analyte sensor mentioned in claim 1, wherein an area of the first electrode group is not less than an area of the second electrode group.

8. According to the micro analyte sensor mentioned in claim 1, wherein when the first electrode group is prematurely terminated, the second electrode group switches to the first frequency and provides the detection signal instead.

9. A continuous analyte monitoring device, comprising:

a bottom case for mounting on a surface;

a sensor unit comprising a base and at least one micro analyte sensor of claim 1, wherein the micro analyte sensor is fixed on the base, and the sensor unit is mounted on the bottom case through the base to provide the detection signal;

a transmitter unit, comprising an internal circuit, a transmitter and an electrical connection area, wherein the electrical connection area and the sensor unit are electrically connected, the internal circuit triggers the first electrode group or the second electrode group according to a predetermined frequency, and the transmitter is configured to output analyte parameter information;

a battery for providing electrical energy; and a receiver for receiving and displaying the detection signal.

* * * * *